(12) United States Patent
Berg

(10) Patent No.: US 9,452,075 B2
(45) Date of Patent: Sep. 27, 2016

(54) KNEE BRACE IMPROVEMENT

(71) Applicant: Randy John Berg, St. Cloud, MN (US)

(72) Inventor: Randy John Berg, St. Cloud, MN (US)

(*) Notice: Subject to any disclaimer, the term of this patent is extended or adjusted under 35 U.S.C. 154(b) by 0 days.

(21) Appl. No.: 14/563,758

(22) Filed: Dec. 8, 2014

(65) Prior Publication Data

US 2015/0223960 A1 Aug. 13, 2015

Related U.S. Application Data

(60) Provisional application No. 61/937,882, filed on Feb. 10, 2014.

(51) Int. Cl.
*A61F 5/00* (2006.01)
*A61F 5/01* (2006.01)

(52) U.S. Cl.
CPC ...... *A61F 5/0123* (2013.01); *A61F 2220/0008* (2013.01)

(58) Field of Classification Search
CPC ............... A61F 5/0123; A61F 5/0125; A61F 2005/0179; A61F 2005/0169
USPC ...................................... 602/16, 26
See application file for complete search history.

(56) References Cited

U.S. PATENT DOCUMENTS

| | | | | |
|---|---|---|---|---|
| 3,976,057 A * | 8/1976 | Barclay | ................ | A61F 5/0125 482/113 |
| 4,606,542 A * | 8/1986 | Segal | .................... | A61F 5/0125 482/105 |
| 5,203,754 A * | 4/1993 | Maclean | ............ | A63B 21/0004 482/121 |
| 6,117,097 A * | 9/2000 | Ruiz | ..................... | A61F 5/0109 602/20 |
| 2007/0232972 A1* | 10/2007 | Martinez | ............... | A61F 5/0125 602/16 |
| 2011/0207585 A1* | 8/2011 | Burns | .................. | A61F 5/0123 482/124 |

* cited by examiner

*Primary Examiner* — Kristen Matter

(57) ABSTRACT

This invention is an elastic mechanism that extends and retracts during motions of the knee so that it maintains tension in a generally rearward direction on the area of the head of the tibia throughout the range of motion of the knee. The structure is anchored to a stable superior part of the body, above a height of contour, by an attachment which can be a belt, girdle, garment, suspenders or a combination of these attachments. The elastic mechanism attaches inferiorly to a number of connection mechanisms which connect to both sides of a hinged rigid knee brace near the tibial head, below the hinges of the knee brace.

3 Claims, 1 Drawing Sheet

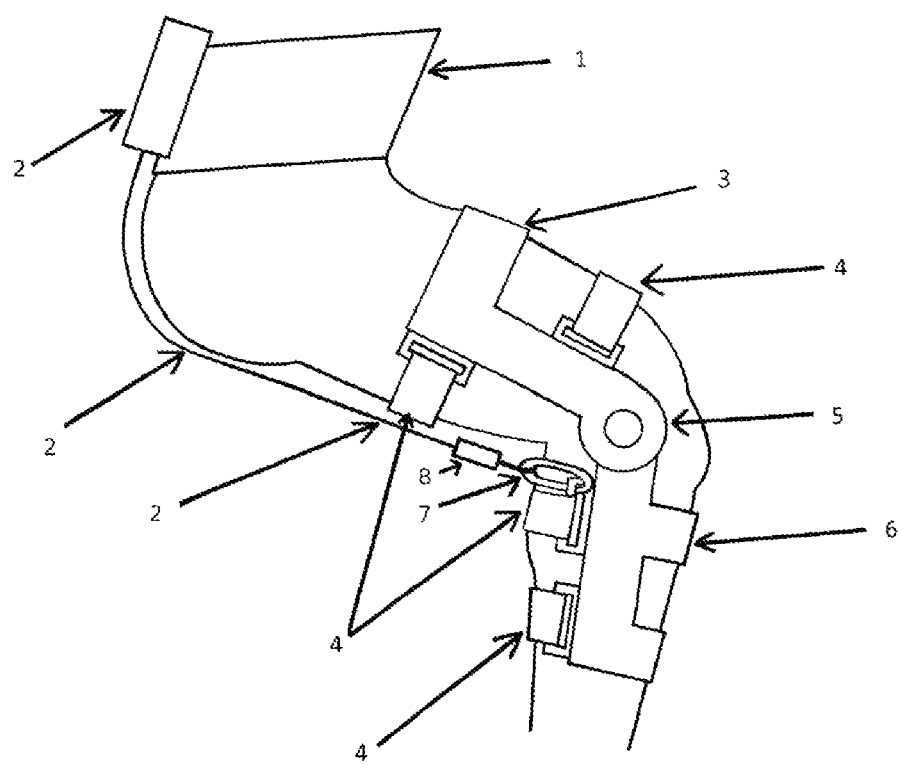

KNEE BRACE IMPROVEMENT

CROSS-REFERENCE TO RELATED APPLICATIONS

This application relates to provisional application 61/937,882 dated Feb. 10, 2014

BACKGROUND OF THE INVENTION

1. Field of the Invention

The present invention relates to a device used to stabilize a knee joint, improve the performance characteristics of a knee joint and improve the security of a knee joint in humans when used with a knee brace.

2. Description of Prior Art

Current knee braces addressing anterior cruciate ligament problems typically comprise two rigid support elements which are connected by a pair of hinges on either side of the knee. The brace is typically secured to the leg by a number of straps. Some knee braces further have spring type elements to limit the free extension of the knee near its limit of range of motion. Some other knee braces have spring type elements to assist resistance to flexion of the knee.

No current knee braces apply elastic rearward tension to area of the tibial head throughout the vast majority of the range of motion of the knee. The knee is very much more stable in the case of a stretched, partially torn or functionally absent anterior cruciate ligament if the tibial head can be tensioned in a rearward direction throughout the range of motion of the knee.

SUMMARY OF THE INVENTION

The principal object of the present invention is to provide a device for use in sporting activities and for other activities, which enhances the stabilizing effects and the protective effects of a knee brace by providing rearward tension to the area of the head of the tibia. It is also an object of the present invention to provide such a device which is simple, light weight and inexpensive to construct and wear.

This objective can be accomplished by attaching an elastic mechanism to both sides of the rear area of a hinged rigid knee brace, below the hinges (near the head of the tibia) and securing the elastic mechanism to a stable, superior part of the body, above a height of contour, with a belt, girdle, garment, suspenders or a combination of these attachments.

DESCRIPTION OF THE PREFERRED EMBODIMENT

The preferred embodiment of this invention comprises: an attachment mechanism, a waist belt and an elastic mechanism. The elastic mechanism further comprises a cable, a helical compression spring and a spring housing. The spring housing has a spring seat for the spring. The spring seat has an opening for the cable to slide through in the center of the spring seat. The spring housing is firmly attached to the waist belt at the end of the housing which has the fixed spring seat. The cable attaches to a washer or other enlargement at or beyond the free end of the spring. The washer is larger than the central lumen of the helical compression spring. The cable passes through the central lumen of the spring and exits through the central hole in the spring seat such that when the cable is tensioned from beyond the exit hole end of the spring seat, the washer compresses the helical compression spring The cable further extends from the spring seat, down the back of the leg, to an attachment mechanism. The attachment mechanism connects to two additional cable elements which extend to the area of the tibial head on each side of the knee and terminate with clasps which are used to attach to a knee brace on both sides, below the hinges. The attachment mechanism is a metal casting which comprises an adjustable attachment for the cable which extends from the spring seat. This adjustable attachment comprises a drilled hole for the cable of the elastic mechanism to pass through and a number of set screws that compress the cable within the drilled hole. The set screws allow for adjustment of cable length in order to fit various sized people. The cast attachment mechanism is a bicycle brake cable spreader yoke for center pull brakes with cable elements and clasps attached at the knee brace end.

The spring housing and spring seat are a metal pneumatic quick coupler male end with a length of polyurethane tubing slid over and adhesively bonded to the largest diameter of the coupler. The helical compression spring sits inside the polyurethane tubing. The threaded end of the pneumatic quick coupler is capped with a threaded plumbing end cap. The plumbing end cap is centrally drilled to a diameter to allow insertion of a length of bicycle brake cable housing. A short length of rubber tubing between the coupler and end cap is used to compress and hold the inserted bicycle brake cable housing when the end cap is tightened.

The brake cable housing functions to smooth the directional change of the cable from horizontal (along the belt) to vertical (down the back of the leg), reducing frictional wear. The directional change is further smoothed by running the brake cable housing between two wheels which are riveted to the waist belt and covered by a rigid plate which is drilled for and secured by the same rivets. This limits the turn radius of the cable. The spring housing and spring seat are attached to a waist belt by pipe hanger straps and rivets.

The waist belt is a weight lifting belt which provides a stable anchoring platform for the elastic mechanism.

BRIEF DESCRIPTION OF THE DRAWING

The drawing shows one embodiment of the invention as a lateral view of a leg which is wearing a hinged rigid knee brace. The knee brace has a rigid upper sleeve #3 and a rigid lower sleeve #6. A hinge #5 on each side of the knee connects the two rigid sleeves. The brace has a number of straps #4 for securing the brace to the leg. Each side of the lower rigid sleeve of the brace is connected by a clasp #7 to the attachment mechanism #8. The attachment mechanism connects the bilateral clasps to the cable of the rearward tensioning elastic mechanism #2. The rearward tensioning elastic mechanism #2 is anchored to a waist belt #1.

DETAILED DESCRIPTION OF THE INVENTION

As shown in the drawing, the preferred device includes an elastic mechanism anchored to a stable superior part of the body, above a height of contour, by an attachment which can be a belt, girdle, garment, suspenders or a combination of these attachments. The elastic mechanism attaches inferiorly to a number of connection mechanisms which connect to both sides of a hinged rigid knee brace near the tibial head, below the hinges of the knee brace. The cable of the elastic mechanism can be adjusted in length to fit various sized people to provide a generally rearward tension to the area of the head of the tibia, throughout the majority of range of motion of the knee. This replaces or supplements a significant function of the original anterior cruciate ligament. The components used to fabricate the preferred embodiment are previously described in the description of the preferred embodiment.

The preferred embodiment description is not meant to limit the claim to that embodiment. The elastic mechanism could alternatively be a number of elastomeric bands, tubes or sheets of a different configuration of springs and cables.

The invention claimed is:

1. An improvement for a hinged rigid knee brace comprising:

the hinged rigid knee brace comprising an upper rigid portion adapted to be attached to a thigh of a wearer; a lower rigid portion adapted to be attached to a calf of the wearer; a hinge on a left side of the hinged rigid knee brace; and a hinge on a right side of the hinged rigid knee brace, the hinges connecting the upper and lower rigid portions;

a belt configured to be worn above the waist of the wearer; and an elastic mechanism, the elastic mechanism being attached at a first end to a back end of the belt and attached at a second end to connection mechanisms that flexibly connect the elastic mechanism to both the left and right sides of the hinged rigid knee brace below the hinges; wherein the elastic mechanism stretches and retracts throughout hinging motion of the hinged rigid knee brace, maintaining tension in a rearward direction upon the lower rigid portion of the hinged rigid knee brace near the hinges.

2. The improvement of claim 1, wherein the elastic mechanism comprises elastomer.

3. The improvement of claim 1, wherein the elastic mechanism comprises a spring.

* * * * *